| United States Patent [19]
Petty

[11] Patent Number: 4,761,494
[45] Date of Patent: Aug. 2, 1988

[54] PREPARATION OF CYANOMETHYL ESTERS

[75] Inventor: Walter L. Petty, Watsonville, Calif.

[73] Assignee: E. I. Du Pont de Nemours and Company, Wilmington, Del.

[21] Appl. No.: 124,867

[22] Filed: Nov. 23, 1987

Related U.S. Application Data

[63] Continuation-in-part of Ser. No. 896,987, Aug. 15, 1986, abandoned, which is a continuation-in-part of Ser. No. 642,297, Aug. 20, 1984, abandoned.

[51] Int. Cl.$^4$ .................. C07C 120/00; C07C 121/66
[52] U.S. Cl. .................................................... 558/398
[58] Field of Search ........................................ 558/398

[56] References Cited

U.S. PATENT DOCUMENTS

| | | | |
|---|---|---|---|
| 3,917,621 | 11/1975 | Kroposki et al. | 546/25 |
| 4,062,968 | 12/1977 | Fujimoto et al. | 424/275 |
| 4,283,414 | 8/1981 | Harney et al. | 560/101 X |
| 4,291,057 | 9/1981 | Wheeler | 560/152 X |
| 4,390,710 | 1/1983 | Manner | 549/441 |
| 4,526,727 | 7/1985 | Petty | 558/398 |
| 4,560,515 | 12/1985 | Stoutamire et al. | 260/465 D |

FOREIGN PATENT DOCUMENTS 0132392 1/1985 European Pat. Off. .

OTHER PUBLICATIONS

Fieser et al., "Reagents for Organic Synthesis", vol. 3, (1972), pp. 118–119, Wiley–Interscience, N.Y.
Fieser et al., "Reagents for Organic Synthesis", vol. 4, (1974), p. 416, Wiley–Interscience, N.Y.
Morrison & Boyd, "Organic Chemistry", (1959), pp. 474–475, Allyn & Bacon, Inc., Boston, U.S.A.
Kamijo et al., Chem. Pharm. Bull., 31 (10), 1983, pp. 3724–3727.
Kamijo et al., C.A., 100:120462g (1984).

*Primary Examiner*—Joseph Paul Brust
*Attorney, Agent, or Firm*—James A. Costello

[57] ABSTRACT

Cyanomethyl esters are prepared by reacting a carboxylic acid halide with an alpha-hydroxynitrile, a molar excess of a hydrogen halide acceptor and a catalytic amount of a tertiary-aminopyridine or N-methylimidazole.

4 Claims, No Drawings

PREPARATION OF CYANOMETHYL ESTERS

CROSS-REFERENCE TO RELATED APPLICATIONS

This is a continuation-in-part of U.S. Ser. No. 896,987, filed on Aug. 15, 1986, now abandoned, which was a continuation-in-part of U.S. Ser. No. 642,297, filed on Aug. 20, 1984, now abandoned.

BACKGROUND OF THE INVENTION

1. Field of the Invention

The present invention relates to the preparation of cyanomethyl esters by reacting a carboxylic acid halide with an alpha-hydroxynitrile in the presence of certain amines and a minor amount of water impurity.

2. State of the Art

It is known to prepare cyanomethyl esters by reacting a carboxylic acid halide with an alpha-hydroxynitrile in the presence of a molar excess of a tertiary amine hydrogen halide acceptor. However, when this reaction is conducted in the presence of minor amounts of water (usually present as impurities in one or more of the ingredients of the reaction), technical difficulties and an unsatisfactorily impure product cyanomethyl ester can arise because free carboxylic acid is formed which then reacts with the carboxylic acid halide to form a relatively unreactive carboxylic acid anhydride byproduct, thereby reducing the yield of desired cyanomethyl ester, which is also contaminated by the byproduct anhydride. The anhydride is not readily removed from the ester by simple conventional procedures, such as extraction or distillation. Thus, it is highly desirable to eliminate this anhydride from the product produced in the presence of water.

SUMMARY OF THE INVENTION

The present invention is directed to a process for preparing a cyanomethyl ester which comprises treating a carboxylic acid halide with an alpha-hydroxynitrile in the presence of a minor amount of water, a molar excess of tertiary amine hydrogen halide acceptor and a catalytic amount of a tertiary aminopyridine of N-methylimidazole. In the presence of these latter catalysts and excess alpha-hydroxynitrile, any anhydride that is formed by hydrolysis of the carboxylic acid halide is rapidly converted to the desired ester and an equivalent amount of carboxylic acid, which can be removed by either extraction or distillation. Thus, an ester relatively free of anhydride contamination can be prepared even in the presence of minor amounts of water present as an impurity.

More specifically, this invention concerns a process for the preparation of the ester S-alpha-cyano-3-phenoxybenzyl R,S(or S)-alpha-isopropyl-4-chlorophenylacetate or of a mixture enriched therein from reactants that contain a water impurity, the process consisting of treating racemic or S-alpha-isopropyl-4-chlorophenylacetic acid chloride with a molar excess of S-alpha-cyano-3-phenoxybenzyl alcohol or a racemic mixture enriched therein, in the presence of an inert solvent, a molar excess of a tertiary amine hydrogen halide acceptor and a catalytic amount of a 4-tertiary-aminopyridine catalyst of the formula

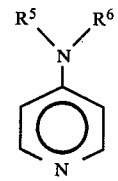

wherein:

$R^5$ and $R^6$ are independently selected from $C_1$ to $C_{24}$ alkyl, $C_3$ to $C_{24}$ alkenyl and $C_3$ to $C_{24}$ alkynyl groups, or phenylmethyl and phenylethyl groups in which the phenyl moiety can be further substituted by one to five $C_1$ to $C_4$ alkyl groups, or $R^5$ and $R^6$ can be taken together as a $-(CH_2)_n-$alkylene chain wherein each carbon individually can be substituted with one to two groups selected from $C_1$ to $C_{12}$ alkyl, $C_2$ to $C_{12}$ alkenyl and $C_2$ to $C_{12}$ alkynyl, and n is an integer from 4 to 6, the water impurity amounting to no more than 0.2 moles per mole of carboxylic acid chloride starting material and the ester product containing less than about 3 weight percent of carboxylic acid anhydride caused by the presence of the water impurity.

The more preferred catalysts are 4-(dimethylamino)pyridine, 4-pyrrolidinopyridine, 4-piperidinopyridine and 4-(4-methyl-1-piperidinyl)pyridine. Most preferred, for its solubility in hydrogen solvents, is 4-(4-methyl-1-piperidinyl)pyridine.

DETAILS OF THE INVENTION

The process of this invention is useful for preparing esters from any optically-active acid halides (which do not contain substituent groups that react with base). For example, the acid halide can be that of an acyclic, alicyclic, aromatic (aryl or aralkyl) or hetero(aromatic) acid.

The reaction is conducted in the absence of a solvent or in the presence of an inert organic solvent, which is suitably selected from non-hydroxylic solvents such as hydrocarbons, chlorinated hydrocarbons, ethers and the like. Suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between about 40° C. to 65° C., between about 60° C. to 80° C. or between about 80° C. to 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring. For example, carbon tetrachloride, chloroform, dichloromethane, 1,2-dichloroethane, trichloroethane, perchloroethylene, chlorobenzene and 1,3- or 1,4-dichlorobenzene. Ethers are generally those containing from 4 to 6 carbon atoms such as diethyl ether, methyl tert-butyl ether and diisopropyl ether. Preferably, the solvent is an aromatic hydrocarbon solvent, such as toluene.

The reaction with acid halide is preferably conducted in the presence of a molar excess of hydrogen halide acceptor, which is a secondary or tertiary amine including amines such as triethylamine, pyridine, N,N-dimethylbenzylamine or 2,6-lutidine, and the like, added slowly, with agitation, and usually after the other reactants are well mixed. Preferably, the halide acceptor is N,N-dimethylbenzylamine.

In the preparation of the cyanomethyl esters by the process of the present invention, it is necessary to have a molar excess of alcohol to acid halide at the end of the reaction in order that any residual anhydride can be converted to ester. Therefore, a molar ratio of alcohol to acid halide can be from about 10:1 to 1:1.1 and preferably from about 5:1 to 1:1.1, the latter ratio depending upon how much acid halide is lost to hydrolysis.

In the preparation of the cyanomethyl ester, the temperature can be varied widely. At normal pressure, for example, the temperature of reaction can suitably be from about 0° C. to 70° C., but is preferably from about 10° C. to 40° C., more or less.

Separation and recovery of the product cyanomethyl ester are achieved by conventional methods, including crystallization and the like.

The process of the invention is useful for preparing cyanomethyl esters from any carboxylic acid halide which does not contain substituted groups which would react with the base. For example, the acid halides are conventionally known in the art and include any acyclic, alicyclic, aromatic or hetero(aromatic) acid halides and preferably have the Formula I

wherein X is a halogen atom; $R^1$ and $R^2$ are each independently selected from the group alkyl, aralkyl, alkoxy, aryloxy, alkylthio, alkylsulfonyl, arylthio, and arylsulfonyl containing from 1 to 10 carbon atoms and cycloalkyl containing 3 to 7 ring carbon atoms, or, when taken together with the carbon atom to which they are attached, form a cycloalkyl group containing 3 to 7 ring carbon atoms; $R^2$ is also an alkenyl or alkynyl group containing from 2 to 10 carbon atoms; a naphthyl group; a phenyl group; or a heterocyclic group containing 5 or 6 ring atoms, one of which is oxygen, sulfur or nitrogen and the remainder are carbon atoms, or is an amino group disubstituted by one or two acyl groups, or alkyl containing up to 10 carbon atoms. The $R^1$ and $R^2$ groups can be optionally substituted by one or more halogens of atomic numbers 9 to 35, an alkyl, haloalkyl or cycloalkyl group containing up to 7 carbon atoms, an alkenyl or haloalkenyl group of 2 to 4 carbon atoms, a haloalkoxy or alkoxy group of 1 to 4 carbon atoms, a haloalkylthio or alkylthio group of 1 to 4 carbon atoms or equivalent kinds of substituents. Acid halides of Formula I are preferred in which X is chlorine or bromine.

One class of acid halides are of pyrethroid acids, including those of U.S. Pat. Nos. 4,024,163; 4,062,968; 4,220,591; 3,835,176; 4,243,819; 4,316,913 and 4,199,595. Examples of such acid halides include those of Formula I in which $R^1$ is isopropyl or cyclopropyl; $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy, haloalkoxy in which the halogens are bromine, chlorine or fluorine and the alkyl groups contain 1 or 4 carbon atoms, or $R^1$ and $R^2$ together with the carbon atom to which they are attached form a cyclopropyl group of the formula

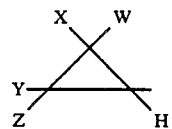

in which W, X, Y and Z are each independently a hydrogen atom, a halogen atom of atomic numbers 9 to 35, or an alkyl group containing 1 to 4 carbon atoms, or Y and Z each independently is an alkyl group containing 1 to 4 carbon atoms, W is a hydrogen atom and X is pentahaloethyl, 2,2-dihalovinyl, isobutenyl, perhalomethylvinyl, 2-phenyl-2-halovinyl, 2-phenyl-1,2,2-trihaloethyl or (alkoxyimino)methyl, or ((cycloalkylalkoxy)imino)methyl of 1 to 10 carbon atoms. For example, the acid halide is isopropyl(4-chlorophenyl)acetyl chloride, isopropyl(4-(difluoromethoxy)phenyl)acetyl chloride, isopropyl((4-trifluoromethyl-3-chlorophenyl)(benzyloxycarbonyl)amino)acetyl chloride, 2,2-dimethyl-3-(2,2-dichlorovinyl)cyclopropanecarbonyl chloride, 2,2-dimethyl-3-(2,2-dibromovinyl)cyclopropanecarbonyl chloride, 2,2-dimethyl-3-(1,2-dibromo-2,2-dichloroethyl)cyclopropanecarbonyl chloride, 1-(4-ethoxyphenyl)-2,2-dichlorocyclopropanecarbonyl chloride, 2,2-dimethyl-3-(2-(trifluoromethyl)-2-chlorovinyl)cyclopropanecarbonyl chloride, 2,2-dimethyl-3-((isobutoxyimino)methyl)cyclopropanecarbonyl chloride, 2,2-dimethyl-3-((neopentoxyimino)methyl)cyclopropanecarbonyl chloride, 2,2-dimethyl-3-(((cyclobutylmethoxy)imino)methyl)cyclopropanecarbonyl chloride, or chrysanthemyl chloride, and the like.

Preferably, in Formula I, $R^1$ is isopropyl and $R^2$ is a phenyl group optionally substituted by halogen, an alkyl or haloalkyl group of 1 to 4 carbon atoms or an alkoxy or haloalkoxy group containing 1 to 4 carbon atoms, preferably at the para position, especially useful are 4-chlorophenyl, 4-(difluoromethoxyphenyl), 4-methylphenyl, 4-tert-butylphenyl and the like.

Any racemic or optically-active alpha-hydroxynitrile is useful (provided it does not contain substituent groups which would otherwise interfere with the reaction). Preferably, the alpha-hydroxynitrile is a symmetrical or non-symmetrical, racemic or optically-active alpha-hydroxynitrile of Formula II

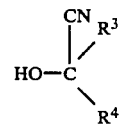

wherein $R^3$ is an optionally-substituted hydrocarbyl or heterocyclic group; and $R^4$ is an optionally-substituted hydrocarbyl group or a hydrogen atom or $R^3$ and $R^4$ together with the carbon atom to which they are attached form a carbocyclic group as denoted by the dotted line.

The hydrocarbyl groups represented by $R^3$ and $R^4$ in the Formula II can be, for example, an alkyl, a cycloalkyl or an aryl group of up to 20 carbon atoms, preferably up to 10 carbon atoms, or $R^3$ in the Formula II can be a carboxylic or an O or S heterocyclic aryl group containing up to 14 carbon atoms. Examples of carboxylic aryl groups are phenyl, 1-naphthyl, 2-naphthyl and 2-anthryl groups. Heterocyclic aromatic groups are derived from heteroaromatic compounds which are defined as in, Kirk-Othmer, "Encyclopedia of Chemical Technology", Second Edition, Volume 2 (1963), page 702. They can be obtained by replacement of one or more carbon atoms of a carboxylic aromatic compound by a heteroatom selected from O or S, and also include those heterocyclic compounds having five-membered rings which show aromatic characteristics and are mentioned on page 703 of said volume.

Optional substituents include one or more halogen atoms having an atomic number from 9 to 35, inclusive, or an alkyl, alkenyl or alkoxy group containing 1 to 6 carbon atoms, each optionally substituted by one or more halogen atoms, optionally substituted phenoxy, phenyl, benzyl or benzoyl and equivalent kinds of substituents. Illustrative examples of the alpha-hydroxynitriles include alpha-hydroxy-alpha-methylbutyronitrile, alpha-hydroxy-alpha-methylbenzene-acetonitrile, alpha-hydroxyisobutyronitrile and the like.

Preferably, the alpha-hydroxynitrile can be racemic or have the R- or S-configuration, and therefore, include either the racemic, R- or, preferably S-alpha-hydroxynitrile of Formula III

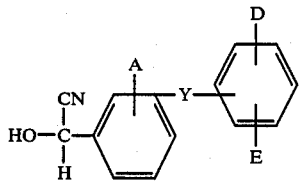

wherein Y is O, CH$_2$, or C(O); each A, D and E independently is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of 9 to 35, inclusive. Preferably, each A, D or E independently is a hydrogen atom, a fluorine atom, a chlorine atom, a methyl group, a trifluoromethyl group or a methoxy group. Preferably, one of D and E is a hydrogen atom. An especially preferred subclass of S-alpha-hydroxynitriles are those of the formula above in which D is a hydrogen atom and A and E each independently is a fluorine atom or a hydrogen atom, and, preferably, when either A or E is fluorine, each is located at the 4-position of the ring relative to the aromatic substituent. Especially suitable alcohols are those wherein A is a fluorine atom at the 4-position or a hydrogen atom and E is a hydrogen atom.

Examples of alpha-hydroxynitriles of the above formula include S-alpha-cyano-3-phenoxybenzyl alcohol, S-alpha-cyano-4-fluoro-3-phenoxybenzyl alcohol, S-alpha-cyano-3-(4-fluorophenoxy)benzyl alcohol, and their corresponding enantiomers.

In one embodiment of the invention, an S-alpha-cyano-3-phenoxybenzyl alcohol or mixture enriched therein is treated with an S-alpha-isopropylphenylacetic acid chloride or an optionally-substituted chiral cyclopropanecarboxylic acid chloride to give an optically-active cyanomethyl ester or a mixture enriched therein.

The alpha-isopropylphenylacetic acid halides or a mixture enriched therein are generally known as in U.S. Pat. Nos. 3,996,244 and 4,199,596 and Japanese Pat. Nos. 54/3035 and 54/27,532.

The alpha-hydroxynitriles (cyano alcohols) or a mixture enriched in an optical isomer thereof are disclosed in U.S. Pat. Nos. 3,835,176 and 4,273,727. The enriched forms can be prepared by prior art methods which are not relevant to the method of this invention. For example, the method of U.S. Pat. No. 4,594,198 comprises treating the appropriate aldehyde with a source of hydrogen cyanide in a substantially water-immiscible, aprotic solvent and in the presence of a cyclo-D-phenylalanyl-D-histidine dipeptide catalyst.

The 4-tertiary-aminopyridines and N-methylimidazole are conventional chemicals and are usually used in catalytic amounts of about 0.01 to 2.0 weight percent based upon the carboxylic acid halide and, preferably, about 0.05 to 1.5 weight percent. It can be useful for the tertiary amine acid halide acceptor to also be the 4-tertiary-aminopyridine or N-methylimidazole. In such cases, the material is present in a molar excess based upon the acid halide. The 4-tertiary-amino-pyridines include 4-(dimethylamino)pyridine, 4-(4-methyl-1-piperidinyl)pyridine and the like.

The cyanomethyl esters prepared by the process of this invention have the Formula IV:

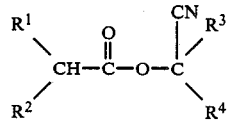

Such esters are generally known in the art; see Francis et al., J. Chem. Soc., 95, pages 1403 to 1409 (1909); and are known in their optical forms from U.S. Pat. Nos. 4,151,195; 4,239,737; 4,328,167 and 4,133,826 and British Pat. No. 2,014,137. Preferably, the product is an optically-active ester, such as S-alpha-cyano-3-phenoxybenzyl S-alpha-isopropyl-4-chloro-phenylacetate, S-alpha-cyano-3-phenoxybenzyl S-alpha-isopropyl-4-(difluoromethoxy)phenylacetate, S-alpha-cyano-3-phenoxybenzyl (1R,cis)-3-(1,2-dibromo-2,2-dichloroethyl)-2,2-dimethylcyclopropanecarboxylate, S-alpha-cyano-3-phenoxybenzyl (1R,cis)-2,2-dimethyl-3-(isobutoxyiminomethyl)cyclopropanecarboxylate, and the like, or a mixture enriched in such an optically-active ester.

One embodiment of the invention is directed to a process for the preparation of an optically-active cyanomethyl ester or a mixture enriched therein and comprises treating a carboxylic acid halide with an optically-active, optionally-substituted alpha-hydroxynitrile (S-alpha-cyanobenzyl alcohol), or mixture enriched therein, in the presence of a minor amount of water, a molar excess of a hydrogen halide acceptor and a catalytic amount of a tertiary-aminopyridine or N-methylimidazole to realize the corresponding ester, with retention of optical configuration in the alcohol moiety.

Another embodiment of the invention is a process for the preparation of an S-alpha-cyano-3-phenoxybenzyl R,S(or S)alpha-isopropylphenylacetate in substantially pure form, or of a mixture enriched therein, which comprises treating a racemic or S-alpha-isopropylphenylacetic acid halide with an S-alpha-cyano-3-phenoxybenzyl alcohol or a mixture enriched therein to give the phenylacetate, with retention of optical configuration in the acid and alcohol moieties.

Phenylacetate "alpha" or "A-alpha" products (wherein "alpha" denotes R,S-acid S-alcohol pair and "A-alpha" denotes S-acid S-alcohol single isomer) include those having the Formula V:

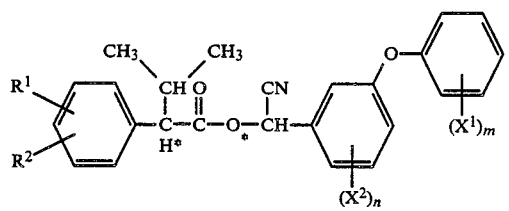

wherein $R^1$ is a hydrogen atom, a halogen atom having an atomic number from 9 to 53, inclusive, or an alkyl group containing 1 to 4 carbon atoms or an alkoxy group containing 1 to 2 carbon atoms, each optionally substituted by one or more halogen atoms having an atomic number from 9 to 53, inclusive, $R^2$ is a hydrogen atom or a methyl group, $X^1$ and $X^2$ each independently is a halogen atom having an atomic number from 9 to 35, inclusive, or is methyl, and m and n each independently is 0 or 1, and * denotes the asymmetric carbon atom in the acid and alcohol moieties, respectively.

Preferably, $R^1$ is a halogen atom or an optionally halogenated alkyl or alkoxy group as defined above, for example, $R^1$ is a chlorine or fluorine atom, methyl, ethyl, isopropyl, tert-butyl, methoxy, ethoxy, difluoromethoxy or trifluoromethoxy and $R^2$ is a hydrogen atom. $R^1$ is preferably located at the meta- or para-position relative to the benzylic carbon atom in the acid moiety. Preferably, $R^1$ is located at the para-position. Also preferred are those phenylacetates of Formula V wherein m is 0 and n is 0 or 1, and $X^2$ is located in the 4-position relative to the benzylic carbon atom in the alcohol moiety. Especially useful are those phenylacetates of Formula V wherein n is 0 or when n is 1 then $X^2$ is fluorine at the 4-position. It is further preferred to prepare a phenylacetate product of a material of Formula V in which $R^1$ is chlorine or difluoromethoxy, $R^2$ is a hydrogen atom, $X^2$ is fluorine and m is 0 and n is 0 or 1.

The presence of a 4-tertiary-aminopyridine catalyst reduces the amount of carboxylic acid anhydride impurity in the optically-active cyanomethyl ester to less than about 3 weight percent when the amount of water impurity in the starting materials amounts to about 0.005 moles to 0.2 moles per mole of carboxylic acid chloride starting material. While the instant invention solves the problem of acid anhydride contamination, the water impurity present still consumes some of the valuable carboxylic acid chloride starting material. Therefore, it is preferred that the amount of water impurity not exceed 0.1 moles per mole of carboxylic acid chloride for best results.

EXAMPLES

The following embodiments are provided for the purpose of illustrating the invention and should not be regarded as limiting it in any way. The identity of the products was confirmed by infrared and nuclear magnetic resonance spectral analyses as necessary.

EXAMPLE 1

A mixture of 2.92 g of R,S-alpha-isopropyl-p-chlorophenylacetic acid chloride and 1.90 g of S-alpha-cyano-3-phenoxybenzyl alcohol containing 0.00715 g of water were combined with 8.9 g of toluene and stirred at 20° C. while 1.81 g of N,N-dimethylbenzylamine containing 0.09 weight percent of 4-(dimethylamino)pyridine was metered in over 1 hour. The reaction mixture was stirred for two additional hours, washed twice with dilute aqueous hydrochloric acid to remove N,N-dimethylbenzylamine hydrochloride and 4-(dimethylamino)pyridine and stripped of solvent under vacuum to give S-alpha-cyano-3-phenoxybenzyl R,S-alpha-isopropyl-4-chlorophenylacetate containing 1.1 weight percent of R,S-alpha-isopropyl-4-chlorophenylacetic anhydride.

The experiment was repeated except in the presence of 0.02715 g of water to give the desired ester containing 0.06 weight percent of anhydride.

EXAMPLE 2

Following procedures similar to those of Example 1 and with the same reactants, 2.92 g of R,S-acid chloride, 3.18 g of S-alpha-cyano alcohol containing 0.00196 g of water were reacted in the presence of the N,N-dimethylbenzylamine as halide acceptor containing the catalytic amount of 4-(dimethylamino)pyridine to give the desired ester, essentially free of anhydride.

EXAMPLE 3

A mixture of 2.92 g of R,S-alpha-isopropyl-4-chlorophenyl-acetic acid chloride and 2.86 g of S-alpha-cyano-phenoxybenzyl alcohol containing 0.0218 g of water in 8.4 g of toluene was stirred at 20° C. while 1.80 g of N,N-dimethylbenzylamine containing 0.1 weight percent of 4-(4-methyl-1-piperidinyl)pyridine was metered in over 1 hour. The reaction mixture was stirred for one additional hour. The product ester was recovered as described in Example 1 and contained 0.6 weight percent of anhydride.

EXAMPLE 4

A mixture of 165.6 g of S-alpha-isopropyl-4-chlorophenyl-acetic acid, 163.2 g of S-alpha-cyano-3-phenoxybenzyl alcohol and 396.4 g of toluene containing about 0.42 g of water was stirred at 10° C., and a mixture of 104.4 g of N,N-dimethylbenzylamine, 0.11 g of 4-(4-methyl-1-piperidinyl)pyridine, and 250.2 g of toluene containing about 0.93 g of water was metered in during 1 hour. The reaction mixture was stirred for an additional 3 hours. The product S,S ester was recovered as described in Example 1 and was essentially free of anhydride.

The following Examples further illustrate the effect of a 4-tertiary-aminopyridine catalyst in reducing the amount of carboxylic acid anhydride impurity caused by the presence of water in the esterification reaction mixture.

EXAMPLE 5

N,N-dimethylbenzylamine (approximately 1.05 molar equivalents) in toluene was added over 1 hour to a stirred mixture of R,S-alpha-isopropyl-p-chlorophenyl-acetic acid chloride (1.00 molar equivalent), S-alpha-cyano-3-phenoxybenzyl alcohol (1.02 molar equivalents) and water (0.031 molar equivalents) in toluene at 20° C. The mixture was allowed to react for 2 additional hours. The mixture was then washed with dilute aqueous hydrochloric acid and stripped of solvent under vacuum. The isolated S-alpha-cyano-3-phenoxybenzyl R,S-alpha-isopropyl-4-chlorophenylacetate product was found by infrared spectroscopy to contain 4.0 weight percent of R,S-alpha-isopropyl-4-chlorophenylacetic anhydride.

The process was repeated as described, except that 4-(dimethylamino)pyridine (0.1 weight percent based on N,N-dimethylbenzylamine) was added to the N,N-dimethylbenzylamine feed solution. The isolated S-alpha-cyano-3-phenoxybenzyl R,S-alpha-isopropyl-4-chlorophenylacetate product from this run was found by infrared spectroscopy to contain only 1.1 weight percent of R,S-alpha-isopropyl-4-chloro-phenylacetic anhydride.

EXAMPLE 6

N,N-dimethylbenzylamine (approximately 1.05 molar equivalents) in toluene was added over 1 hour to a stirred mixture of R,S-alpha-isopropyl-p-chlorophenylacetic acid chloride (1.00 molar equivalent), S-alpha-cyano-3-phenoxybenzyl alcohol (1.11 molar equivalents) and water (0.119 molar equivalents) in toluene at 20° C. The mixture was allowed to react for 2 additional hours. The mixture was then washed with dilute aqueous hydrochloric acid and stripped of solvent under vacuum. The isolated S-alpha-cyano-3-phenoxybenzyl R,S-alpha-isopropyl-4-chlorophenylacetate product was found by infrared spectroscopy to contain 6.0 weight percent of R,S-alpha-isopropyl-4-chlorophenylacetic anhydride.

The process was repeated as described, except that 4-(dimethylamino)pyridine (0.1 weight percent based on N,N-dimethylbenzylamine) was added to the N,N-dimethylbenzylamine feed solution. The isolated S-alpha-cyano-3-phenoxybenzyl R,S-alpha-isopropyl-4-chlorophenylacetate product from this run was found by infrared spectroscopy to contain only 0.06 weight percent of R,S-alpha-isopropyl-4-chlorophenylacetic anhydride.

What is claimed:

1. A process for the preparation of the ester S-alpha-cyano-3-phenoxy-benzyl R,S(or S)-alpha-isopropyl-4-chlorophenylacetate or of a mixture enriched therein from reactants that contain a water impurity, the process consisting of treating racemic or S-alpha-isopropyl-4-chlorophenylacetic acid chloride with a molar excess of S-alpha-cyano-3-phenoxybenzyl alcohol or a racemic mixture enriched therein, in the presence of an inert solvent, a molar excess of a tertiary amine hydrogen halide acceptor and a catalytic amount of a 4-tertiary aminopyridine catalyst of the formula

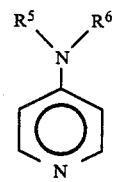

wherein:
$R^5$ and $R^6$ are independently selected from $C_1$ to $C_{24}$ alkyl, $C_3$ to $C_{24}$ alkenyl and $C_3$ to $C_{24}$ alkynyl groups, or phenylmethyl and phenylethyl groups in which the phenyl moiety can be further substituted by one to five $C_1$ to $C_4$ alkyl groups, or $R^5$ and $R^6$ can be taken together as a $-(CH_2)_n-$ alkylene chain wherein each carbon individually can be substituted with one to two groups selected from $C_1$ to $C_{12}$ alkyl, $C_2$ to $C_{12}$ alkenyl and $C_2$ to $C_{12}$ alkynyl, and n is an integer from 4 to 6, the water impurity amounting to no more than about 0.2 moles per mole of carboxylic acid chloride starting material and the ester product containing less than about 3 weight percent of carboxylic acid anhydride caused by presence of the water impurity.

2. A process according to claim 1 wherein the amount of water impurity is 0.005 to 0.10 moles per mole of carboxylic acid chloride.

3. A process according to claim 1 wherein the 4-tertiary-aminopyridine catalyst is 4-(dimethylamino)pyridine, 4-pyrrolidinopyridine, 4-piperidinopyridine or 4-(4-methyl-1-piperidinyl)pyridine.

4. A process according to claim 3 wherein the 4-tertiary-aminopyridine catalyst is 4-(4-methyl-1-piperidinyl)pyridine.

* * * * *